United States Patent [19]

Tabei et al.

[11] Patent Number: 5,403,943
[45] Date of Patent: Apr. 4, 1995

[54] CHLORO-TERMINATED POLYSILANE

[75] Inventors: Eiichi Tabei; Shigeru Mori, both of Kawasaki, Japan

[73] Assignee: Shin-Etsu Chemical Company, Limited, Tokyo, Japan

[21] Appl. No.: 125,859

[22] Filed: Sep. 24, 1993

Related U.S. Application Data

[63] Continuation-in-part of Ser. No. 6,487, Jan. 21, 1993, Pat. No. 5,292,415.

[30] Foreign Application Priority Data

Jan. 21, 1992 [JP] Japan .................................. 4-30103
Mar. 27, 1992 [JP] Japan .................................. 4-101804

[51] Int. Cl.$^6$ .............................................. C07F 7/08
[52] U.S. Cl. ................................................. 556/430
[58] Field of Search ..................................... 556/430

[56] References Cited

PUBLICATIONS

Zhang, et al., (1984) Journal of Polymer Science-Polymer Chem. Edition 22:159-170.
R. West, (1986) Journal of Organometallic Chemistry 300:327-346.
Sakaurai et al, Kagaku to Kogyo, Chemistry & Industry, vol. 42, No. 4, pp. 744-747 (1985).
Kumada, et al., (1964) Journal of Organometallic Chemistry, 2:478-484.
Ishikawa, et al., (1970) Journal of Organometallic Chemistry 23:63-69.
Wolff, et al., (1987) Applied Organometallic Chemistry 1:7-14.

*Primary Examiner*—Paul F. Shaver
*Attorney, Agent, or Firm*—Birch, Stewart, Kolasch & Birch

[57] ABSTRACT

The invention provides a novel chloro-terminated polysilane of the formula:

$$Cl[(R^1R^2Si)_n(R^3R^4Si)_m]_kCl \qquad (1)$$

wherein $R^1$, $R^2$ and $R^3$ are alkyl and aryl groups, $R^4$ is a monovalent hydrocarbon group having 2 to 12 carbon atoms selected from substituted and unsubstituted alkyl and aryl groups, n, m and k are numbers in the range: $0 \leq n \leq 10$, $0 < m \leq 10$, $n+m \geq 10$, and $k \geq 1$, especially $k \geq 5$. It is prepared by exposing a high-molecular weight polysilane in chlorinated hydrocarbon to ultraviolet radiation in an inert gas atmosphere.

13 Claims, No Drawings

CHLORO-TERMINATED POLYSILANE

CROSS REFERENCE TO RELATED APPLICATION

This application is a continuation-in-part of application Ser. No. 8/006,487, filed on Jan. 21, 1993, now U.S. Pat. No. 5,292,415, the entire contents of which are hereby incorporated by reference.

BACKGROUND OF THE INVENTION

1. Field of the Invention

This invention relates to $\alpha,\omega$- chloro terminated polysilane capable of accepting any desired functional group and useful as a source material for forming co-polymers with other polymers.

2. Prior Art

Most industrial processes for preparing polysilanes utilize coupling reaction of dihalogenosilanes with alkali metals as reported in Journal of Polymer Science: Polymer Chemistry Edition, Vol. 22, 159–170 (1984) and Journal of Organometallic Chemistry, Vol. 300, 327 (1986). These processes produce polysilanes in the form of mixtures of cyclic polymers and halo- or hydrogen-terminated polymers. It is difficult to quantitatively obtain terminally modified polymers from these mixtures.

With respect to the synthesis of single end modified polysilanes, Sakurai et al. attempted living polymerization from polymers containing a disilane unit for introducing hydrogen or carboxylic acid as well as copolymerization of such polymers with polymethyl methacrylate (PMMA) as reported in Kagaku to Kogyo (Chemistry & Industry), Vol. 42, No. 4, 744. This attempt, however, has several industrial problems including limited type of substituents and limited availability of monomers.

Exemplary synthesis of both and single end reactive polysilanes is reported in Journal of Organometallic Chemistry, Vol. 2, 478–484 (1964) and Journal of Organometallic Chemistry, Vol. 23, 63–69 (1970). More specifically, chloro-terminated oligosilanes can be prepared by reacting permethyloligosilanes with acetyl chloride in the presence of aluminum chloride. Also chloro-terminated oligosilanes can be prepared by reacting phenyl-terminated oligo silanes with hydrogen chloride or chlorosilane in the presence of aluminum chloride. These chloro-terminated oligosilanes, however, have a low polymerization degree.

SUMMARY OF THE INVENTION

Therefore, an object of the present invention is to provide a novel and improved chloro-terminated polysilane with a high degree of polymerization capable of accepting any desired functional group and suitable as a source material for forming copolymers with other polymers.

Focusing on the reaction that on exposure to ultraviolet (UV) radiation, polysilanes decompose and convert to those of a lower molecular weight while yielding highly reactive silylene and silyl radicals as reported in Applied Organometallic Chemistry, Vol. 1, 7–14 (1987), the inventors have found that when high-molecular weight polysilanes are photo-decomposed by selecting a chlorinated hydrocarbon as a solvent prone to chlorine withdrawal and exposing the polysilanes to UV radiation in the chlorinated hydrocarbon, silyl radicals generate and then form chloro-terminated polysilanes having a high polymerization degree.

More specifically, coupling reaction of dichlorosilane with alkali metal yields a high-molecular weight polysilane which is a mixture of a cyclic polymer and a halo- or hydrogen-terminated polymer as previously mentioned. When such a polysilane is exposed to UV radiation, the cyclic polymer opens its ring and converts into a chloro-terminated polysilane through photo-decomposition. At the same time, the halo- or hydrogen-terminated polymer remains unreactive where it has a terminal halogen atom, but where it has a terminal hydrogen atom, the hydrogen atom is replaced by a chlorine atom under the action of light or heat. As a result, from high-molecular weight polysilane, there is obtained a chloro-terminated polysilane having a lower molecular weight which is dictated by the dose of UV radiation.

Accordingly, the present invention provides a both end chloro-terminated polysilane of the formula:

$$Cl[(R^1R^2Si)_n(R^3R^4Si)_m]_kCl \qquad (1)$$

wherein $R^1$, $R^2$ and $R^3$ are independently monovalent hydrocarbon groups having 1 to 12 carbon atoms selected from substituted or unsubstituted alkyl and aryl groups, $R^4$ is a monovalent hydrocarbon groups having 2 to 12 carbon atoms selected from substituted or unsubstituted alkyl and aryl groups, letters n, m and k are numbers in the range: $0<n\leq 10$, $0<m\leq 10$, $n+m\geq 10$, and $k\geq 1$.

DETAILED DESCRIPTION OF THE INVENTION

The chloro-terminated polysilane of the present invention is represented by formula (1).

$$Cl[(R^1R^2Si)_n(R^3R^4Si)_m]_kCl \qquad (1)$$

In formula (1), $R^1$, $R^2$ and $R^3$ which may be identical or different, are monovalent hydrocarbon groups having 1 to 12 carbon atoms, preferably 1 to 10 carbon atoms selected from substituted or unsubstituted alkyl and aryl groups. The alkyl groups include methyl, ethyl and propyl groups and the aryl groups include phenyl and tolyl groups. $R^4$ is a monovalent hydrocarbon group having 2 to 12 carbon atoms selected from substituted or unsubstituted alkyl and aryl groups. Examples of $R^4$ are ethyl, propyl, butyl, n-hexyl, cyclohexyl and phenyl. If $R^1$ to $R^4$ are all methyl groups in formula (1), that is the compound has the following formula:

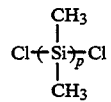

$$Cl{-}(\underset{\underset{CH_3}{|}}{\overset{\overset{CH_3}{|}}{Si}}){_p}Cl$$

it is not dissolved into any solvents including toluene, xylene and THF and is impractical. Refer to Japanese Patent Application Kokai 61-238790. Letters n, m and k are numbers in the range: $0\leq n\leq 10$, $0<m\leq 10$, $n+m\geq 10$, and $k\geq 1$. Preferably, k is 5 or more, especially 10 or more, in order that the polysilane exert photoconductivity and other desired properties. The term chloro-terminated means that the polysilane is terminated with chlorine at both ends of its molecular chain unless otherwise stated.

The chloro-terminated polysilanes of formula (1) are soluble in toluene, xylene, and THF (tetrahydrofrane). If $R^1$, $R^2$ and $R^3$ are all alkyl groups and $R^4$ is also an alkyl group except methyl group, such polysilanes are soluble in an alkane such as hexane. However, the chloro-terminated polysilanes are difficultly soluble in alcohols such as methanol, ethanol and isopropyl alcohol, and ketones such as acetone.

The chloro-terminated polysilane of formula (1) is prepared by first effecting coupling reaction of a dichlorosilane with an alkali metal such as sodium for forming a polysilane. The dichlorosilane used herein should preclude the use of dimethyldichlorosilane alone. The polymer obtained by the reaction between dimethyldichlorosilane and sodium (Na) is not dissolved into a solvent such as toluene, xylene and THF and has a low polymerization degree. Aromatic group-containing dichlorosilanes such as methylphenyldichlorosilane and ethylphenyldichlorosilane, dichlorosilanes having a $C_2$ or higher aliphatic group such as methylethyldichlorosilane, methylpropyldichlorosilane, methyl-hexyldichlorosilane and dihexyldichlorosilane may be used alone or in admixture of two or more. The coupling reaction results in a polysilane of the general formula (2):

wherein $R^1$, $R^2$, $R^3$ and $R^4$ are as defined above, $0 \leq n'$, $0 < m'$, $10 \leq n' + m'$, preferably $30 \leq n' + m'$. It preferably has a number average molecular weight (Mn) of 1,000 to 1,000,000, more preferably 5,000 to 1,000,000.

Next, the polysilane is dissolved in a chlorinated hydrocarbon solvent and exposed to UV radiation in an inert gas atmosphere. Polysilanes having a high molecular weight is not dissolved into the chlorinated hydrocarbon solvent and therefore this method can not be employed therefor. Examples of the chlorinated hydrocarbon used herein include dichloromethane, chloroform, carbon tetrachloride, 1,2 -dichloroethane, 1,1,2 -trichloroethane, and 1,1,2,2 -tetra-chloroethane alone or in admixture of two or more.

Preferably, the polysilane is dissolved in a chlorinated hydrocarbon to form a solution at a concentration of about 1 to 20% by weight, more preferably about 1 to 10% by weight. The polysilane solution is sealingly filled in a Pyrex® or quartz reaction tube and irradiated with UV radiation in an inert gas atmosphere using a high pressure mercury lamp (312 nm), for example. The inert gas may be nitrogen or argon gas though not limited thereto. The dose of UV radiation may be properly determined since the resulting chloro-terminated polysilane has a molecular weight which depends on the UV dose.

After exposure to a predetermined dose of UV, the reaction solution is concentrated to ½ to 1/5 in volume. Hexane is added to the concentrate such that about 150 grams of hexane is available per 10 grams of the polysilane, thereby causing the chloro-terminated polysilane (Mn≧1,000) to precipitate. Through filtration and drying, the end chloro terminated polysilane is obtained as white powder.

The thus obtained chloro-terminated polysilane according to the present invention has reactive chlorine at both ends thereof and therefore, hydroxyl groups can be introduced at the both ends by hydrolysis or any other suitable technique. The resulting hydroxy-terminated polysilane may, in turn, be copolymerized with other polymers to form copolymers such as dialkylhydroxy-terminated polysilanes and dialkylvinylsiloxy-terminated polysilanes. In this regard, the chloro-terminated polysilane of the invention is a useful source material for forming copolymers with other polymers.

EXAMPLE

Examples of the present invention are given below by way of illustration and not by way of limitation. All percents are by weight. Mn and Mw are number and weight average molecular weights, respectively.

Examples 1–5

Methylphenylpolysilane having Mn=24,000 and Mw/Mn=3.32 was previously prepared by coupling reaction of methylphenyldichlorosilane with sodium. 7.0 grams of methylphenylpolysilane was dissolved in 133 grams of carbon tetrachloride. The solution had a concentration of 5%. In a nitrogen gas atmosphere, a Pyrex reaction tube with a diameter of 15 mm was filled with the polysilane solution, closed with a plug, and exposed to UV radiation (312 nm) in a dose of 1 J/cm² using a high-pressure mercury lamp. The reaction solution was concentrated to about 50 grams. Addition of 100 grams of hexane to the solution caused precipitation of a chloro-terminated polysilane of the following formula (3). It was isolated by filtration and dried, obtaining a white powder (Example 1).

The procedure of Example 1 was repeated except that the UV dose was changed to 2, 3, 5 and 10 J/cm², yielding white powders (Examples 2–5).

Table 1 reports the Mn, Mw/Mn and yields of these white powders. Their chlorine contents as measured by titration are also reported together with the theoretical values.

TABLE 1

| | | Chloro-terminated polysilane | | | | |
|---|---|---|---|---|---|---|
| Example | UV dose (J/cm²) | Mn | Mw/Mn | Yield (%) | Cl (%) Found | Cl (%) Calc. |
| 1 | 1 | 15,970 | 2.34 | 77 | 0.45 | 0.45 |
| 2 | 2 | 12,220 | 1.94 | 65 | 0.54 | 0.58 |
| 3 | 3 | 11,980 | 1.93 | 63 | 0.58 | 0.59 |
| 4 | 5 | 8,300 | 1.70 | 60 | 0.84 | 0.86 |
| 5 | 10 | 4,600 | 1.47 | 52 | 1.49 | 1.53 |

Example 6

Methylphenylpolysilane having Mn=15,900 and Mw/Mn=10 was previously prepared by coupling reaction of methylphenyldichlorosilane with sodium. 0.5 grams of methylphenylpolysilane was dissolved in 9.5 grams of dichloromethane. The solution had a concentration of 5%. In a nitrogen gas atmosphere, a Pyrex reaction tube with a diameter of 15 mm was filled with the polysilane solution, closed with a plug, and exposed to UV radiation (312 nm) in a dose of 0.5 J/cm² using a high-pressure mercury lamp. The reaction solution was concentrated to about 2 grams. Addition of 20 grams of hexane to the solution caused precipitation of the product. It was isolated by filtration and dried, obtaining a chloro-terminated polysilane as a white powder.

Example 7

The procedure of Example 6 was repeated except that the UV dose was changed to 1 J/cm$^2$, yielding a white powder.

Example 8

Methylphenylpolysilane having Mn=15,900 and Mw/Mn=10 was previously prepared by coupling reaction of methylphenyldichlorosilane with sodium. 0.5 grams of methylphenylpolysilane was dissolved in 9.5 grams of 1,2-dichloroethane. The solution had a concentration of 5%. In a nitrogen gas atmosphere, a Pyrex reaction tube with a diameter of 15 mm was filled with the polysilane solution, closed with a plug, and exposed to UV radiation (312 nm) in a dose of 0.5 J/cm$^2$ using a high-pressure mercury lamp. The reaction solution was concentrated to about 2 grams. Addition of 20 grams of hexane to the solution caused precipitation of the product. It was isolated by filtration and dried, obtaining a chloro-terminated polysilane as a white powder.

Example 9

The procedure of Example 8 was repeated except that the UV dose was changed to 1.5 J/cm$^2$, yielding a white powder.

Examples 10–12

The procedure of Example 6 was repeated except that the solvent was changed to chloroform, 1,1,2-trichloroethane and 1,1,2,2-tetrachloroethane, yielding chloro-terminated polysilanes as white powders (Examples 2–5).

Table 2 reports the Mn, Mw/Mn and yields of these white powders. Their chlorine contents as measured by titration are also reported together with the theoretical values.

centration of 5%. In a nitrogen gas atmosphere, a Pyrex reaction tube with a diameter of 15 mm was filled with the polysilane solution, closed with a plug, and exposed to UV radiation (312 nm) in a dose of 1 J/cm$^2$ using a high-pressure mercury lamp. The reaction solution was concentrated to obtain a white powder as a product.
Mn: 16,000 (calculated as polystyrene)
Mw/Mn: 2.50
Yield: 70%
Cl(%): Found 0.40% (Calc. 0.44%)

Example 14

The polysilane (II) having the following formula:

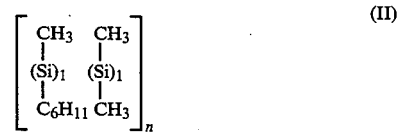

and having Mn=25,000 and Mw/Mn=3.0 was previously prepared by coupling reaction of methylhexyldichlorosilane and dimethyldichlorosilane with sodium. 7.0 grams of the polysilane (II) was dissolved in 133 grams of carbon tetrachloride. The solution had a concentration of 5%. In a nitrogen gas atmosphere, a Pyrex reaction tube with a diameter of 15 mm was filled with the polysilane solution, closed with a plug, and exposed to UV radiation (312 nm) in a dose of 1 J/cm$^2$ using a high-pressure mercury lamp. The reaction solution was concentrated to obtain a white powder as a product.
Mn: 17,200 (calculated as polystyrene)
Mw/Mn: 2.90
Yield: 79%
Cl(%): Found 0.40%
(Calc. 0.41%)

Example 15

TABLE 2

| Example | Methylphenylpolysilane (g) | Solvent Type | Amount (g) | UV dose (J/cm$^2$) | Chloro-terminated polysilane Mn* | Mw/Mn | Cl content (ppm) Found | Cacl. | Yield (%) |
|---|---|---|---|---|---|---|---|---|---|
| 6 | 0.5 | dichloromethane | 9.5 | 0.5 | 13500 | 4.94 | 4900 | 5260 | 82 |
| 7 | 0.5 | dichloromethane | 9.5 | 1.0 | 10800 | 3.59 | 6200 | 6570 | 74 |
| 8 | 0.5 | 1,2-dichloroethane | 9.5 | 0.5 | 15000 | 7.00 | 4300 | 4730 | 76 |
| 9 | 0.5 | 1,2-dichloroethane | 9.5 | 1.5 | 11500 | 6.05 | 5500 | 6170 | 64 |
| 10 | 0.5 | chloroform | 9.5 | 0.5 | 13300 | 4.51 | 5000 | 5340 | 71 |
| 11 | 0.5 | 1,1,2-trichloroethane | 9.5 | 0.5 | 13000 | 5.20 | 5100 | 5460 | 65 |
| 12 | 0.5 | 1,1,2,2-tetrachloroethane | 9.5 | 0.5 | 12100 | 4.82 | 5300 | 5870 | 74 |

*calculated as polystyrene

Example 13

The polysilane (I) having the following formula:

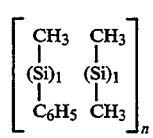

and having Mn=31,000 and Mw/Mn=3.32 was previously prepared by coupling reaction of methylphenyldichlorosilane and dimethyldichlorosilane with sodium. 7.0 grams of the polysilane (I) was dissolved in 133 grams of carbon tetrachloride. The solution had a con- The polysilane (III) having the following formula:

and having Mn=55,000 and Mw/Mn=2.5 was previously prepared by coupling reaction of dihexyldichlorosilane with sodium. 7.0 grams of the polysilane (III) was dissolved in 133 grams of carbon tetrachloride. The solution had a concentration of 5%. In a nitrogen gas atmosphere, a Pyrex reaction tube with a diameter of 15 mm was filled with the polysilane solution, closed with a plug, and exposed to UV radiation (312 nm) in a dose of 1 J/cm$^2$ using a high-pressure mercury lamp. The reaction solution was concentrated to obtain a white powder as a product.

Mn: 31,000 (calculated as polystyrene)
Mw/Mn: 2.70
Yield: 85%
Cl(%): Found 0.21%
( Calc. 0.23% )

Next, exemplary synthesis of a hydroxy-terminated polysilane from a chloro-terminated polysilane according to the present invention is described.

Reference Example 1

In 100 grams of THF was dissolved 5.0 grams of a chloro-terminated methylphenylpolysilane (Mn=7,500 Mw/Mn=1.57). To the solution, 0.2 grams of triethylamine was added, 3 grams of water was added dropwise, and the mixture was agitated under reflux for 4 hours. At the end of reaction, 100 grams of toluene was added to the reaction solution, which was washed with 100 grams of water three times. The organic layer was dried overnight over calcium chloride. After the desiccant was filtered off, the organic layer was concentrated, obtaining 3.5 grams of a white powder.

The results of analysis of this white powder are shown below which indicate that it is a both end hydroxy-terminated methylphenylpolysilane.

Yield: about 75%
Mn: 7,550 (calculated as polystyrene)
Mw/Mn: 1.64
IR analysis: peak at 3624 cm$^{-1}$ (Si-OH)
OH quantity: 0.0260 mol/100 g (calculated: 0. 0265 mol/100 g)

Reference Example 2

In 300 grams of THF was dissolved 15.0 grams of a chloro-terminated methylphenylpolysilane (Mn=5,600, Mw/Mn=1.66). To the solution, 1.2 grams of triethylamine was added, 10 grams of water was added dropwise, and the mixture was agitated under reflux for 4 hours. At the end of reaction, 300 grams of toluene was added to the reaction solution, which was washed with 300 grams of water three times. The organic layer was dried overnight over calcium chloride. After the desiccant was filtered off, the organic layer was concentrated, obtaining 11.3 grams of a white powder.

The results of analysis of this white powder are shown below which indicate that it is a hydroxy-terminated methylphenylpolysilane.

Yield: about 75%
Mn: 5,620 (calculated as polystyrene)
Mw/Mn: 2.09
IR analysis: peak at 3624 cm$^{-1}$ (Si-OH)
OH quantity: 0.0350 mol/100 g (calculated: 0.0356 mol/100 g)

The process of the present invention facilitates synthesis of chloro-terminated polysilanes having a degree of polymerization of at least 5, especially at least 10. The chloro-terminated polysilanes allow various functional groups to be introduced therein and are useful source materials for forming copolymers with other polymers.

Although some preferred embodiments have been described, many modifications and variations may be made thereto in the light of the above teachings. It is therefore to be understood that within the scope of the appended claims, the invention may be practiced otherwise than as specifically described.

We claim:

1. A chloro-terminated polysilane of the formula:

$$Cl[(R^1R^2Si)_n(R^3R^4Si)_m]_kCl \quad (1)$$

wherein $R^1$, $R^2$ and $R^3$ are independently monovalent hydrocarbon groups having 1 to 12 carbon atoms selected from substituted or unsubstituted alkyl and aryl groups, $R^4$ is a monovalent hydrocarbon group having 2 to 12 carbon atoms selected from substituted and unsubstituted alkyl and aryl groups, letters n, m and k are numbers in the range: $0 \leq n \leq 10$, $0 < m \leq 10$, $n+m \geq 10$, and $k \geq 1$.

2. The chloro-terminated polysilane according to claim 1, wherein $R^1$, $R^2$ and $R^3$ are independently selected from the group consisting of methyl, ethyl and propyl.

3. The chloro-terminated polysilane according to claim 1, wherein $R^1$, $R^2$ and $R^3$ are independently selected from the group consisting of phenyl and tolyl.

4. The chloro-terminated polysilane according to claim 1, wherein $R^4$ is selected from the group consisting of ethyl, propyl, butyl, n-hexyl, cyclohexyl and phenyl.

5. The chloro-terminated polysilane according to claim 1, wherein k is 5 or more.

6. The chloro-terminated polysilane according to claim 1, wherein k is 10 or more.

7. The chloro-terminated polysilane according to claim 1, wherein n=0, m=10 and $R^4$ is an aryl group.

8. The chloro-terminated polysilane according to claim 1, wherein $R^3$ is a methyl group and $R^4$ is a phenyl group.

9. The chloro-terminated polysilane according to claim 1, wherein $R^4$ is an aryl group.

10. The chloro-terminated polysilane according to claim 1, wherein $R^1$, $R^2$ and $R^3$ are methyl groups and $R^4$ is a phenyl group.

11. The chloro-terminated polysilane according to claim 1, wherein $R^4$ is a hexyl group.

12. The chloro-terminated polysilane according to claim 1, wherein $R^1$, $R^2$ and $R^3$ are methyl groups and $R^4$ is a hexyl group.

13. The chloro-terminated polysilane according to claim 1, wherein n=0, m=10 and $R^3$ and $R^4$ are hexyl groups.

* * * * *